United States Patent [19]

Kataoka et al.

[11] Patent Number: 5,325,172
[45] Date of Patent: Jun. 28, 1994

[54] OPTICAL SYSTEM FOR ANALYZING SAMPLES SEPARATED BY A CENTRIFUGAL SEPARATOR

[75] Inventors: Keiji Kataoka; Sadamoto Tachihara; Masakuni Koreeda, all of Katsuta, Japan

[73] Assignee: Hitachi Koki Company Limited, Tokyo, Japan

[21] Appl. No.: 3,914

[22] Filed: Jan. 13, 1993

[51] Int. Cl.$^5$ .................................................. G01B 9/02
[52] U.S. Cl. ........................................ 356/349; 356/128; 356/361; 356/427
[58] Field of Search .................. 356/349, 351, 361, 124, 356/128, 130, 427

[56] References Cited

U.S. PATENT DOCUMENTS

| | | | |
|---|---|---|---|
| 3,391,597 | 7/1968 | Gropper | 356/427 |
| 4,762,414 | 8/1993 | Grego | 356/349 |
| 5,251,009 | 10/1993 | Bruno | 356/128 |

*Primary Examiner*—Samuel A. Turner
*Assistant Examiner*—Russell C. Wolfe
*Attorney, Agent, or Firm*—Lowe, Price, LeBlanc & Becker

[57] ABSTRACT

An optical system is provided with a laser device for emitting a multiplet laser beam with two types of frequencies F1, F2, and a sample rotator on which a reference sample and a test sample containing substances are set for rotating both the test sample and the reference sample to separate the substances contained in the test sample. The test sample and the reference sample are irradiated with the multiplet laser beam one after another to shift the phase of the laser beam. The optical system is further provided with a polarizer for polarizing the multiplet laser beams transmitting through the test sample and the reference sample to produce both a test sample signal with a frequency $\Delta F = F1 - F2$ and a reference sample signal with the frequency $\Delta F$, and a signal analyzer for analyzing a phase difference between the sample signals to determine an index of refraction of the test sample. Therefore, the substances containing in the test sample are specified.

6 Claims, 6 Drawing Sheets

OPTICAL SYSTEM FOR ANALYZING SAMPLES SEPARATED BY A CENTRIFUGAL SEPARATOR

BACKGROUND OF THE INVENTION

1. Field of the Invention

The present invention relates to an optical system in which various substances in a sample are analyzed while rotating the sample in a centrifugal separator, and, in particular, to an optical system in which a sample such as polysaccharide and/or glycoprotein having no light absorption property is analyzed by irradiating the sample with light.

2. Description of the Related Art

A sample containing various substances is generally set in a rotator of a centrifugal separator to optically analyze the various substances. For example, the sample contains polysaccharide and/or glycoprotein which have no light absorption property within a measuring wavelength.

In detail, because each of the various substances has its specific gravity, the various substances are separated from one another by a centrifugal force after the sample is rotated in the rotator. Thereafter, the sample is irradiated with light. In this case, because each of the various substances also has its index of refraction, the phase speed of the light penetrating a substance with a high index of refraction is smaller than that of the light penetrating another substance with a low index of refraction. Therefore, a phase difference occurs between the lights penetrating the substances. Thereafter, the phase difference is analyzed by measuring interference fringes produced by optically interfering the lights to determine the shift of the specific gravity of the sample along a radial direction of the rotator.

2.1. Previously Proposed Art

A conventional optical system for analyzing a sample by utilizing a centrifugal separator is described with reference to FIGS. 1 to 5.

FIG. 1 is a schematic view of a conventional optical system for optically analyzing samples by utilizing a centrifugal separator, and FIG. 2 is a plan view of both a test sample and a reference sample arranged in a sample cell shown in FIG. 1.

As shown in FIG. 1, a conventional optical system 11 is provided with a columnar sample rotator 12 and a plurality of sample cells 13 arranged in hollow portions of the sample rotator 12. The sample rotator 12 is accommodated in a vacuum vessel 14, and the sample cells 13 are positioned at equal distances from a rotation axis 15 of the sample rotator 12. As shown in FIG. 2, both a test sample 16 and a reference sample 17 are arranged side by side in each of the sample cells 13. The test sample 16 consists of various substances which each have both a specific gravity and an index of refraction. The reference sample 17 consists of a reference substance, and an index of refraction of the reference substance is known in advance.

The system 11 is further provided with a mercury lamp 18 for generating monochromatic light 19, an incident light window 20 arranged on a surface of the vacuum vessel 14 for transmitting the monochromatic light 19 generated by the mercury lamp 18 into the vacuum vessel 14 to irradiate the sample cells 13 with the monochromatic light 19, a pair of reflecting mirrors 21, 22 for simultaneously reflecting both a light 23a which transmits through the test sample 16 and a light 23b which transmits through the reference sample 17, a light window 24 arranged on another surface of the vacuum vessel 14 for transmitting the lights 23a, 23b reflected by the reflecting mirror 22 towards the outside of the vacuum vessel 14, and a pair of prisms 25, 26 for producing interference fringes by optically interfering the lights 23a, 23b.

The light 19 generated by the mercury lamp 18 transmits through both the test sample 16 and the reference sample 17 in the sample cell 13 without being absorbed by the samples 16, 17.

In the conventional optical system 11 having the configuration outlined above, an operation for optically analyzing the substances in the test sample 16 is described.

Various types of test samples 16 are initially arranged in the sample cells 13. Also, the sample cells 13 respectively accommodate the same reference sample 17. Thereafter, the sample rotator 12 is rotated about its rotation axis 15. In this case, because the test sample 16 consists of various substances with various specific gravities, the various substances are separated from one another by a centrifugal force generated by the rotation of the sample rotator 12. The centrifugal force acts in a radial direction Rd of the sample rotator 12. That is, substances having small specific gravities are moved towards the rotation axis 15 of the sample rotator 12, and other substances having large specific gravities are moved towards the periphery of the sample rotator 12. Therefore, as shown in FIG. 3, the specific gravity of the test sample 16 is increased from an rotation axis region of the sample rotator 12 to a periphery region. Specifically, in cases where the test sample 16 consists of two main substances, the specific gravity of the test sample 16 is suddenly increased at a middle region.

In addition, because each of the various substances of the test sample 16 has an index of refraction, the index of refraction of the test sample 16 changes along the radial direction Rd of the sample rotator 12 in the same manner as the specific gravity, as shown in FIG. 3.

On the other hand, because the reference sample 17 consists of the reference substance, the specific gravity of the reference sample 17 does not change along the radial direction Rd in the sample cell 13. Also, the index of refraction of the reference sample 17 does not change along the radial direction Rd.

Thereafter, both the test sample 16 and the reference sample 17 in one of the sample cells 13 are simultaneously irradiated from just above with the monochromatic light 19 which is generated by the mercury lamp 18 and transmits through the incident light window 20. Therefore, the phase velocity of the monochromatic light 19 is reduced in both the test sample 16 and the reference sample 17 so that a phase difference occurs between the light 23a transmitting through the test sample 16 and the light 23b transmitting through the reference sample 17. In addition, the monochromatic light 19 is not refracted by either the test sample 16 or the reference sample 17 because the samples 16, 17 are irradiated with the monochromatic light 19 from just above. Also, because the index of refraction of the test sample 16 changes in the sample cell 13 in accordance with the distribution shown in FIG. 3, the degree of the phase difference changes in accordance with the index of refraction of the test sample 16 changing along the radial direction Rd of the sample rotator 12.

Thereafter, the lights 23a, 23b reflect on the reflecting mirrors 21, 22 and transmit the prisms 25, 26 through the light window 24.

FIG. 4 shows the lights 23a, 23b refracted by the prisms 25, 26 in the conventional optical system 11 shown in FIG. 1.

As shown in FIG. 4, the light 23a transmitting through the test sample 16 is refracted by the prism 25, and the light 23b transmitting through the reference sample 17 is refracted by the prism 26. Thereafter, the shifted lights 23a, 23b refracted by the prisms 25, 26 are projected on a screen 27 to show interference fringes.

FIG. 5 shows the interference fringes projected on the screen 27, the interference fringes extending in the radial direction Rd of the sample rotator 12 being shown.

As shown in Fig. 5, the interference fringes consist of curved lines arranged at equal distances from each other and extending in the radial direction Rd. In contrast, the interference fringes would otherwise consist of straight lines arranged at equal distances from each other in cases where the various substances in the test sample 16 is not separated.

Thereafter, the interference fringes projected on the screen 27 is taken a photograph by a camera to analyze the phase distribution of the light 23a transmitting through the test sample 16 by utilizing the interference fringes.

Therefore, the distribution of the index of refraction of the test sample 16 can be relatively measured on the basis of the uniform distribution of the index of refraction of the reference sample 17. In addition, the distribution of the specific gravity of the test sample 16 can be relatively measured so that the various substances contained in the test sample 16 can be specified.

However, because the interference fringes projected on the screen 27 must be taken a photograph, it takes a lot of time to analyze the phase distribution of the light 23a transmitting through the test sample 16 by utilizing the interference fringes. Therefore, it is impossible to efficiently specify the substances contained in many test samples 16.

In addition, because an operator must take reading the interference fringes taken by a photograph with the eye, the accuracy to measure the interference fringes is limited to a scale of one-tenth of the spacing between the interference fringes. Therefore, it is impossible to accurately specify the various substances contained in the test sample 16.

SUMMARY OF THE INVENTION

An object of the present invention is to provide, with due consideration to the drawbacks of such a conventional optical system for analyzing test samples, an optical system for optically analyzing samples separated by a centrifugal separator in which the samples are efficiently analyzed to specify various substances contained in each of the samples with high accuracy.

The above object is achieved by the provision of an optical system for optically analyzing substances contained in a test sample, comprising:

light emitting means for emitting a multiplet beam of light which consists of both a light component with a frequency F1 and another light component with another frequency F2;

a reference sample of which an index of refraction is known;

sample rotating means, in which the test sample and the reference sample are set, for rotating both the test sample and the reference sample to separate the substances contained in the test sample by utilizing a centrifugal force;

optical means for irradiating the test sample and the reference sample one after another with the multiplet beam of light emitted from the light emitting means while rotating the samples by the sample rotating means to shift a phase of a multiplet beam of light L1 transmitting through the reference sample by an angular value $\phi 1$ depending on an index of refraction of the reference sample and to shift a phase of a multiplet beam of light L2 transmitting through the test sample by another angular value $\phi 2$ depending on the index of refraction of the test sample;

light mixing means for mixing both the light components with the frequencies F1, F2 in the multiplet beam of light L1 to produce a combined light LC1 and mixing both the light components with the frequencies F1, F2 in the multiplet beam of light L2 to produce another combined light LC2, the phase of the combined light LC1 being shifted by the angular value $\phi 1$ and the phase of the combined light LC2 being shifted by the angular value $\phi 2$; and phase difference analyzing means for analyzing a phase difference $\Delta\phi = \phi 2 - \phi 1$ by detecting a differential frequency $\Delta F$ contained in both the combined lights LC1, LC2 transmitting from the light mixing means to determine the index of refraction of the test sample separated by the sample rotating means.

In the above configuration of the optical system according to the present invention, the test sample and the reference sample are set in the hollow portions of the sample rotating means before the sample rotating means is rotated at high speed to separate the substances contained in the test sample. Therefore, the substances in the test sample are separated from one another by a centrifugal force generated by the rotation of the sample rotating means. As a result, optical properties such as an index of refraction change in the test sample. On the other hand, because only a substance is contained in the reference sample, the optical properties in the reference sample do not change even though the sample rotating means is rotated at high speed. In addition, the index of refraction Nr of the reference sample is known in advance.

After the sample rotating means is fully rotated enough to separate the substances in the test sample, the test sample and the reference sample are irradiated one after another with a multiplet beam of light emitted from the light emitting means through the optical means while rotating the sample rotating means in a rotational cycle. In this case, the phase of the multiplet beam of light is shifted in the test sample and the reference sample, depending on the index of refraction of the samples. Because the index of refraction of the test sample differs from that of the reference sample, the phase shift $\phi 1$ of the multiplet beam of light L1 transmitting through the reference sample differs from the phase shift $\phi 2$ of the multiplet beam of light L2 transmitting through the test sample.

Thereafter, the light component with the frequency F1 in the multiplet beam of light L1 and the light component with the frequency F2 in the multiplet beam of light L1 are optically mixed by the light mixing means to produce a combined light LC1 in which a light component of a differential frequency $\Delta F = F1 - F2$ is latently contained. Therefore, when the combined light LC1 is detected by a photodetector, the photodetector generates a signal having a frequency component $\Delta F$. Because the frequency $\Delta F$ equals the difference between the frequencies F1, F2, the frequencies F1, F2 of the light L1 is considerably reduced to the differential frequency $\Delta F$. Also, another combined light LC2 is produced from the multiple beam of light L2.

Thereafter, the phase difference $\Delta \phi$ between the combined lights LC1, LC2 is analyzed by the phase difference analyzing means to determine the index of refraction $Nr + \Delta Nr$ of the test sample separated by the sample rotating means.

Accordingly, because the combined light is produced from the multiplet beam of light emitted from the light emitting means by the light mixing means, the index of refraction of each of the substances contained in the test sample can be electrically analyzed so that a large number of test samples can be analyzed.

Also, because the phase difference between the combined lights LC1, LC2 is automatically analyzed by the phase difference analyzing means, a large number of test samples can be efficiently analyzed.

In addition, because the index of refraction of each of the substances is electrically analyzed without taking a photograph, the analysis of the index of refraction can be accomplished with high accuracy.

It is preferred that both the light component with the frequency F1 and the light component with the frequency F2 be polarized at right angles from each other and the light mixing means comprise a polarizer in which both the light component with the frequency F1 and the light component with the frequency F2 are polarized in a direction oriented 45 degrees.

In this case, the combined light LC1 or LC2 is optically formed of the multiplet beam of light.

It is preferred that the phase difference analyzing means comprise a photo detector for detecting one after another both an energy intensity of the combined light LC1 which oscillates at a phase delay time T1 relating to the angular value $\phi 1$ of the phase shift thereof and another energy intensity of the combined light LC2 which oscillates at a phase delay time T2 relating to the angular value $\phi 2$ of the phase shift thereof and generating both a reference sample signal indicating the energy intensity of the combined light LC1 and a test sample signal indicating the energy intensity of the combined light LC2, and a signal analyzer for analyzing a phase delay difference $T2 - T1$ relating to the phase difference $\Delta \phi = \phi 2 - \phi 1$ by utilizing both the reference sample signal and the test sample signal and determining the index of refraction proportional to an product of the phase delay difference $T2 - T1$ and the frequency $\Delta F$.

In this case, because the combined lights LC1, LC2 respectively have the frequency $\Delta F$, the energy intensities of the combined lights are easily detected and are transformed to the sample signals in the photo detector. Also, the phase delay time of each of the combined lights can be analyzed in the signal analyzer.

In addition, the phase difference $\Delta \phi$ is proportional to an product of the phase delay difference $T2 - T1$ and the frequency $\Delta F$, and the index of refraction is proportional to the phase difference $\Delta \phi$. Therefore, the index of refraction of the test sample can be analyzed.

It is preferred that the optical means comprise:
 a focusing unit for focusing the multiplet beam of light emitted from the light emitting means on the sample rotator to irradiate both the reference sample and the test sample with the multiplet beam of which the diameter is reduced; and
 a moving unit for moving the focusing unit in a radial direction of the sample rotating means to entirely irradiate the test sample with tile multiplet beam of light along the radial direction.

In this case, because the focusing unit is moved along the radial direction of the sample rotating means, each of the substances in the test sample separated by the sample rotating means can be irradiated with the multiplet beam of light. Therefore, the shift of the index of refraction of each of the substances in the test sample can be measured along the radial direction. Therefore, the change of the substances separated in the test sample can be analyzed.

It is preferred that the light emitting means be composed of a laser device for emitting a laser beam with a single frequency; and at least one acousto-optic modulator for changing the frequency of the laser beam emitted from the laser device to the multiplet beam of light having a pair of light components with frequencies F1 & F2.

In the above configuration, without utilizing a helium-neon laser device, the multiplet beam of light having a pair of light components with frequencies F1 & F2 is generated in the acousto-optic modulator.

BRIEF DESCRIPTION OF THE DRAWINGS

The objects, features and advantages of the present invention will be apparent from the following description taken in conjunction with the accompanying drawings, in which.

DETAIL DESCRIPTION OF THE PREFERRED EMBODIMENTS

Preferred embodiments of an optical system for optically analyzing test samples separated by a centrifugal separator are described with reference to drawings.

Figure 6:
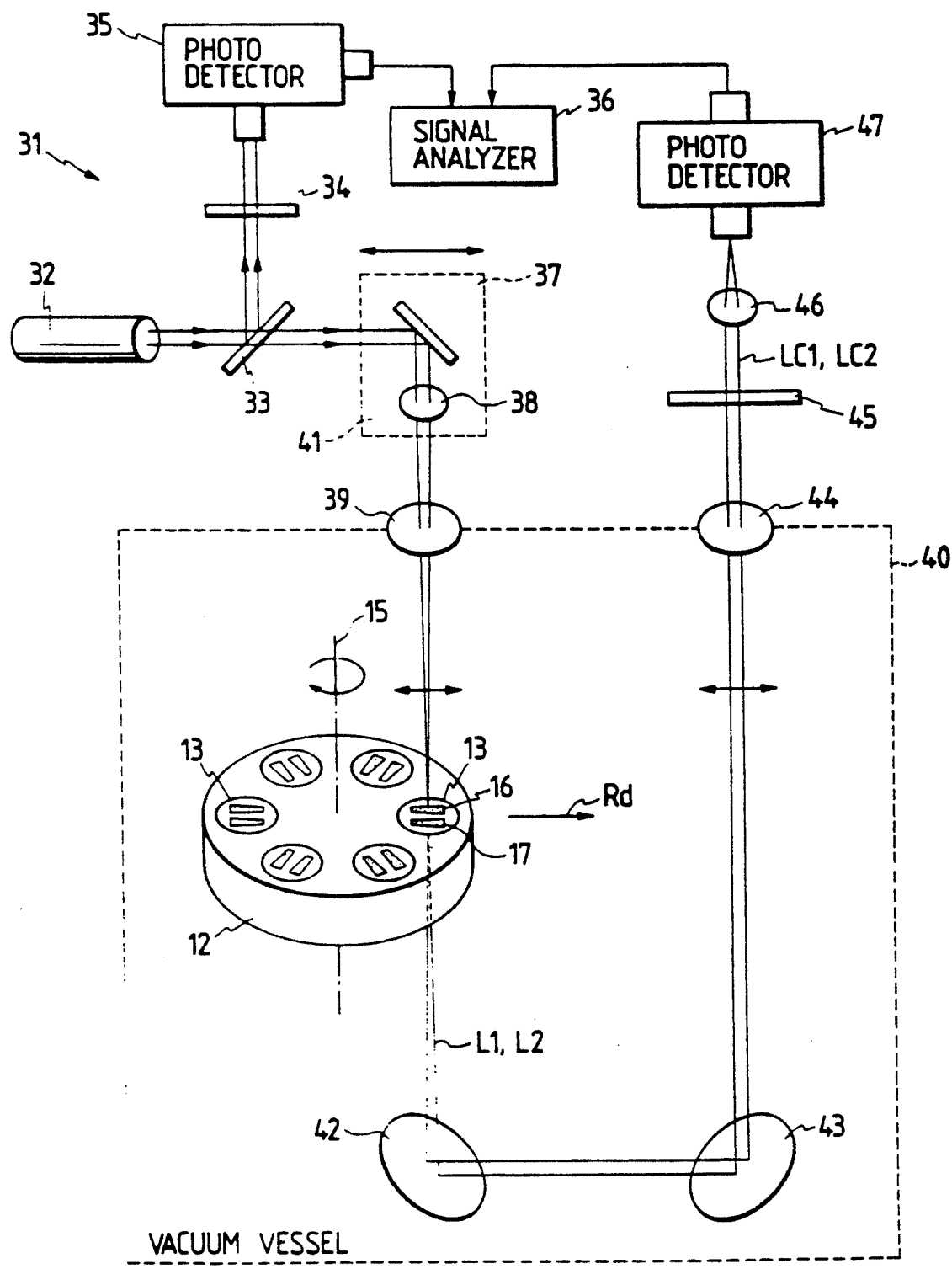
FIG. 6 is a schematic view of an optical system for analyzing samples by utilizing a centrifugal separator according to the present invention.

FIG. 6 is a schematic view of an optical system for optically analyzing samples by utilizing a centrifugal separator according to the present invention.

As shown in FIG. 6, an optical system 31 for analyzing samples by utilizing a centrifugal separator, comprises a helium-neon (He-Ne) laser device 32 for emitting a laser beam having a pair of splitted ( or, non-degenerate ) components of frequencies. The splitted components of the laser beam are generated by splitting degenerate energy states of a He-Ne light emitter in two non-degenerate energy states in a magnetic field in accordance with the Zeeman effect so that the splitted components of the laser beam are polarized at right angles from each other. Also, one of the splitted components has a frequency F1, and another has a frequency F2 (F1>F2). The difference F1−F2 between the frequencies is called a differential frequency $\Delta F=F1-F2$. The value of the differential frequency $\Delta F$ equals about 8 MHz in this embodiment. Moreover, the splitted components with the frequencies F1, F2 are called a multiplet laser beam because the splitted components transmit through the same path in three-dimensional space.

The optical system 31 further comprises a beam splitter 33 for splitting the multiplet laser beam emitted from the laser device 32 in two multiplet laser beams, a first beam polarizer 34 for polarizing one of the multiplet laser beams splitted by the beam splitter 33 in a specific direction, a first photo detector 35 for detecting an energy intensity of the multiplet laser beam polarized by the first beam polarizer 34, and a signal analyzer 36 for analyzing a reference signal Sr indicating the energy intensity detected by the first photo detector 35.

Figure 7:
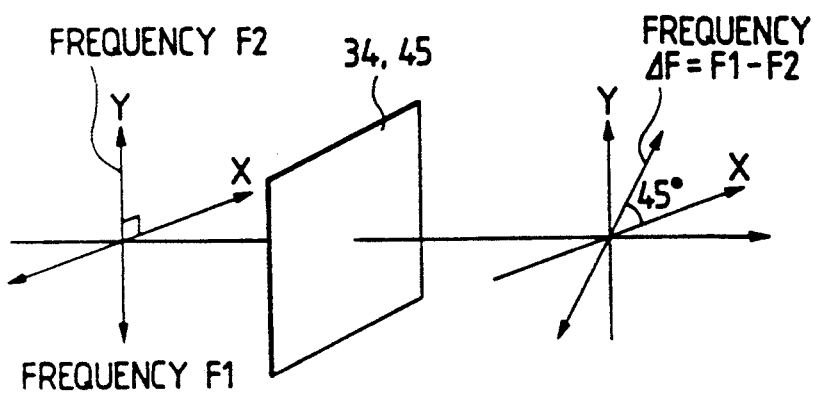
FIG. 7 explanatorily shows an function of a beam polarizer shown in FIG. 6, branched laser beams emitted from a laser device shown in FIG. 6 being polarized by the beam polarizer.

As shown in FIG. 7, when the splitted component with the frequency F1 is polarized in an X-axis direction and the splitted component with the frequency F2 is polarized in a Y-axis direction, both the splitted components of the laser beam are polarized by the first beam polarizer 34 in a direction oriented 45 degrees away from the X-axis and the Y-axis.

On the other hand, an amplitude Ax of the splitted component with the frequency F1 is formulated by an equation (1) as follows.

$$Ax = A*exp\{2*\pi*i*F1*(T-T0)\} \quad (1)$$

Also, an amplitude Ay of the splitted component with the frequency F2 is formulated by an equation (2) as follows.

$$Ay = A*exp\{2*\pi*i*F2*(T-T0)\} \quad (2)$$

Wherein, a symbol i denotes an imaginary unit, a symbol T denotes an elapsed time, and a symbol T0 denotes a phase delay time determined by a propagated distance from the laser device 32 to the first photo detector 35.

Therefore, the energy intensity Ir of the multiplet laser beam detected by the first photo detector 35 is formulated by an equation (3).

$$\begin{aligned}Ir &= |Ax/2^{0.5} + Ay/2^{0.5}|^2 \\ &= A^2*[1 + \cos\{2*\pi*\Delta F*(T-T0)\}]\end{aligned} \quad (3)$$

Figure 8A:
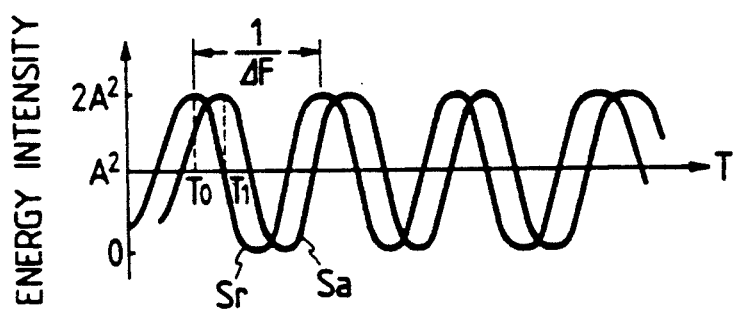
FIGS. 8A, 8B are graphic views of wave forms of a reference signal and sample signals which transmits to a signal analyzer shown in FIG. 6.
Figure 8B:
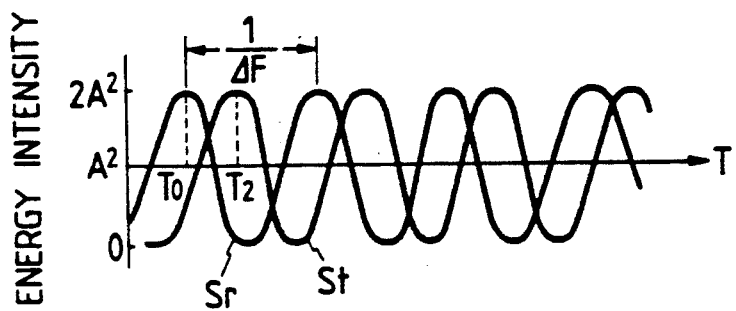

The energy intensity Ir is transmitted to the signal analyzer 36 as the reference signal Sr because the phase of the multiplet laser beam is not shifted by a test sample. As formulated by the equation (3), the energy intensity Ir of the multiplet laser beam is oscillated in a cycle $1/\Delta F$ so that a wave form of the reference signal Sr is shown in a cosine shape in FIGS. 8A, 8B.

The optical system 31 further comprises a first beam mirror 37 for reflecting another of the multiplet laser beams splitted by the beam splitter 33, a first lens 38 for focusing the multiplet laser beam reflected by the first beam mirror 37, a first vacuum vessel window 39 arranged on one of the surface of a vacuum vessel 40 for transmitting the multiplet laser beam focused by the first lens 38 into the vacuum vessel 40, the columnar sample rotator 12 accommodated in the vacuum vessel 40, and the sample cells 13 arranged in hollow portions of the sample rotator 12.

The test sample 16 and the reference sample 17 are arranged in each of the sample cells 13 in the same manner as in the conventional optical system 11. Also, the test sample 16 contains, for example, polysaccharide and/or glycoprotein which have no light absorption property within a measuring wavelength. The multiplet laser beam is focused by the first lens 38 on the sample cells 13 so that the test sample 16 and the reference sample 17 are irradiated with the multiplet laser beam of which the diameter is reduced to about 0.1 mm. Also, because the sample rotator 12 is rotated in a rotational cycle Rc about its rotation axis 15, each of the sample cells 13 is irradiated one after another with the multiplet laser beam. Moreover, the test sample 16 and the reference sample 17 of each of the sample cells 13 are irradiated one after another with the multiplet laser beam.

Therefore, the phase of the multiplet laser beam is shifted in the test sample 16 of one of the sample cells 13 in the rotational cycle Re of the sample rotator 12. An angular value $\phi 2$ of the phase shift of the multiplet laser beam depends on the index of refraction $Nr+\Delta Nr$ of the test sample 16. Also, the phase of the multiplet laser beam is shifted in the reference sample 17 arranged next to the test sample 16 in the rotational cycle Rc of the sample rotator 12. An angular value $\phi 1$ of the phase shift of the multiplet laser beam depends on the index of refraction Nr of the reference sample 1.

In addition, the first beam mirror 37 is integrally formed with the first lens 38 to compose an optical unit 41. Therefore, when the optical unit 41 is moved in the radial direction Rd of the sample rotator 12 both the entire test sample 16 and the entire reference sample 17 are irradiated with the multiplet laser beam along the radial direction Rd of the sample rotator 12.

The optical system 31 further comprises a pair of second beam mirror 42, 43 for reflecting the multiplet laser beam of which the phase is shifted by either the test sample 16 or the reference sample 17, a second vacuum vessel window 44 arranged on another of the surface of the vacuum vessel 40 for transmitting the multiplet laser beam reflected by the beam mirror 42, 43 towards the outside of the vacuum vessel 40, a second beam polarizer 45 for polarizing the splitted components with the frequencies F1, F2 transmitting through the reference sample 17 in a specific direction to produce a combined laser beam and polarizing the splitted components with the frequencies F1, F2 transmitting through the test sample 17 in the specific direction to produce another combined laser beam, a second lens 46 for focusing each of the combined laser beams which are produced from the splitted components polarized by the second beam polarizer 45, and a second photo detector 47 for detecting an energy intensity of each of the combined laser beams focused by the second lens 46.

After the phase of a multiplet laser beam L1 consisting of the splitted components with the frequencies F1, F2 are shifted by the reference sample 17 by the angular value $\phi 1$, the splitted components are polarized by the second beam polarizer 45 in a direction oriented 45 degrees away from the X-axis and the Y-axis, in the same manner as in the first beam polarizer 34. That is, the splitted components are mixed by the second beam polarizer 45 to produce a combined laser beam LC1. Thereafter, an energy intensity Ia of the combined laser beam LC1 is detected by the second photo detector 47. The energy intensity Ia detected by the second photo detector 47 is formulated by an equation (4).

$$Ia = B^2 \ast [1 + \cos\{2\ast \Delta F \ast (T - T1)\}] \quad (4)$$

Wherein, a symbol T1 denotes a phase delay time determined by a propagated distance from the laser device 32 to the second photo detector 47 through the reference sample 17.

Also, after the phase of a multiplet laser beam L2 consisting of the splitted components with the frequencies F1, F2 are shifted by the test sample 16 by the angular value $\phi 2$, the splitted components are polarized by the second beam polarizer 45 in the same manner as the splitted components shifted by the reference sample 17. That is, the splitted components shifted by the test sample 16 are mixed by the second beam polarizer 45 to produce a combined laser beam LC2. Thereafter, an energy intensity It of the combined laser beam LC2 is detected by the second photo detector 47. The energy intensity It detected by the second photo detector 47 is formulated by an equation (5).

$$It = C^2 \ast [1 + \cos\{2\ast\pi\ast \Delta F \ast (T - T2)\}] \quad (5)$$

Wherein, a symbol T2 denotes a phase delay time determined by a propagated distance from the laser device 32 to the second photo detector 47 through the test sample 16. Because the phase velocity of the multiplet laser beam L2 transmitting through the test sample 16 differs from that of the multiplet laser beam L1 transmitting through the reference sample 17, the phase delay time T1 differs from the other phase delay time T2. In cases where the multiplet laser beam L1 is not absorbed in the reference sample 17, a constant $B^2$ equals a constant $A^2$ of the equation (3). Also, in cases where the multiplet laser beam L2 is not absorbed in the test sample 17, a constant $C^2$ equals the constant $A^2$. On the other hand, in cases where the multiplet laser beam LC1 or LC2 is absorbed in the test sample 16 or the reference sample 17, the constant $B^2$ or $C^2$ is smaller than the constant $A^2$.

In addition, because the energy intensities Ia, It are oscillated in an oscillating cycle $1/\Delta F$, the phase delay time T1, T2 of the energy intensities Ia, It can be electrically detected by the signal analyzer 36. Therefore, the energy intensity Ia is transmitted to the signal analyzer 36 as an reference sample signal Sa each time the sample rotator 12 is rotated in the rotational cycle Rc. Also, the energy intensity It is transmitted to the signal analyzer 36 as a test sample signal St each time the sample rotator 12 is rotated in the rotational cycle Rc. As formulated by the equations (4), (5), the energy intensities Ia, It of the combined laser beams LC1, LC2 are oscillated in a cycle $1/\Delta F$ so that wave forms of the sample signals Sa, St are shown in a cosine shape in FIGS. 8A, 8B.

In the signal analyzer 36, the difference in the index of refraction between the test sample 16 and the reference sample 17 is analyzed by measuring a phase delay difference T2−T1 between the phase delay times T1, T2. In detail, in cases where both samples 16, 17 have a thickness D, the reference sample 17 has an index of refraction Nr, the test sample 16 has an index of refraction Nr+$\Delta$Nr, and the multiplet laser beam has an average wave length $\lambda$, the phase of the multiplet laser beam L1 transmitting through the reference sample 17 is shifted by an angular value $\phi 1 = (2\pi/\lambda)\ast Nr \ast D$. Also, the phase of the multiplet laser beam L2 transmitting through the test sample 16 is shifted by another angular value $\phi 2 = (2\pi/\lambda)\ast(Nr+\Delta Nr)\ast D$. Therefore, an optical phase difference $\Delta\phi$ between the angular value $\phi 2$ of the phase shift in the multiplet laser beam L2 and tile angular value $\phi 1$ of the phase shift in the multiplet laser beam L1 is formulated by an equation (6).

$$\Delta\phi = (2\pi/\lambda)\ast \Delta Nr \ast D \quad (6)$$

Also, the optical phase difference $\Delta\phi$ is directly proportional to the phase delay difference T2−T1 so that the optical phase difference $\Delta\phi$ in the combined laser beam LC1 or LC2 is formulated by utilizing the phase delay difference T2−T1.

$$\Delta\phi = 2\pi\ast \Delta F \ast (T2 - T1) \quad (7)$$

Therefore, an equation (8) is obtained on referring to equations (6), (7).

$$\Delta Nr = (T2 - T1)\ast \Delta F \ast (\lambda/D) \quad (8)$$

In this case, because the oscillating cycle $1/\Delta F$ of the signals Sr, Sa, and St is $1/(8\ast 10^6)$ second, the phase delay difference T2−T1 can be measured at accuracy within 1/100 of the oscillating cycle $1/\Delta F$ in accordance with a conventional art. In cases where the thickness D of the samples 16, 17 equals 15 mm and the average wave length $\lambda$ of the multiplet laser beam equals 0.6328 $\mu$m, the difference $\Delta$Nr in the index of refraction between the test sample 16 and the reference sample 17 is analyzed at the accuracy $\pm 4.2\ast 10^{-7}$ (or, $1/100\ast 0.6328\ast 10^{-6}/(15\ast 10^{-3})$) in the signal analyzer 36.

Figure 9A:
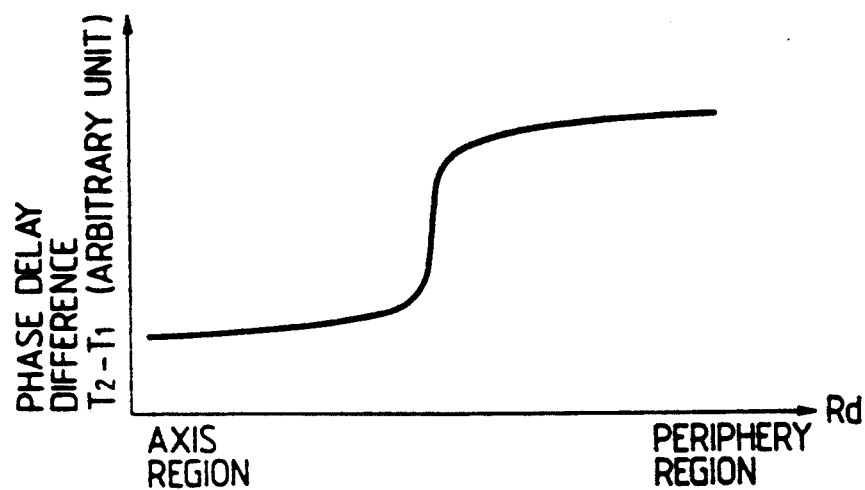
FIG. 9A is a graphic view of a phase delay difference $T2 - T1$ changing along the radial direction Rd of a sample rotator.
Figure 9B:
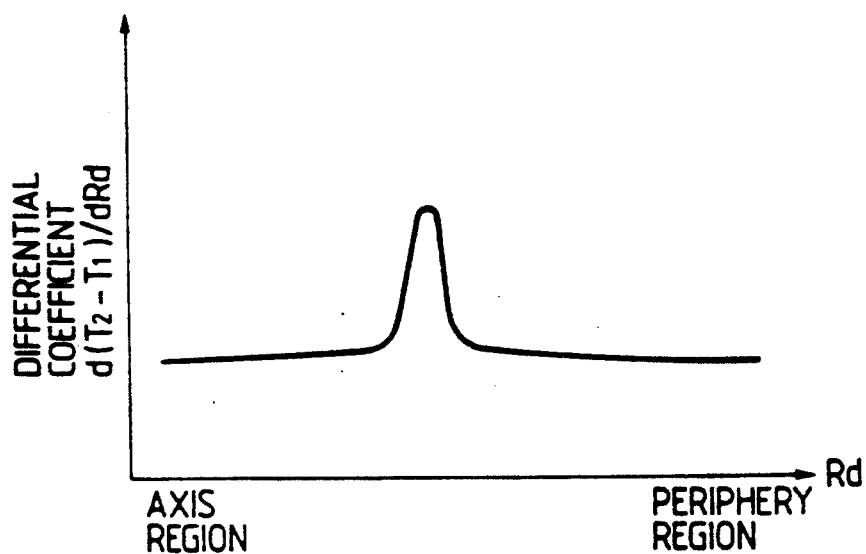
FIG. 9B is a graphic view of a differential coefficient $d(T2 - T1)/dRd$ changing along the radial direction Rd of the sample rotator.

FIG. 9A is a graphic view of the phase delay difference T2−T1 changing along the radial direction Rd of the sample rotator 12, and FIG. 9B is a graphic view of a differential coefficient $d(T2-T1)/dRd$ changing along the radial direction Rd of the sample rotator 12.

As shown in FIG. 9A, because the difference $\Delta$Nr of the index of refraction is directly proportional to the phase delay difference T2−T1 as formulated by the equation (8), the change in the phase delay difference T2−T1 is equivalent to the change in the difference $\Delta$Nr of the index of refraction. Also, because two main substances are contained in the test sample 16, the two main substances are separated at a middle region of the test sample 16. The separation of the substances is expressed by abrupt changes in the differential coefficient d(T2−T1)/dRd shown in FIG. 9B.

Accordingly, the difference ΔNr in the index of refraction can be analyzed at the accuracy $\pm 4.2*10^{-7}$ in the signal analyzer 36. As a result, the separation of the substances contained in the test samples 16 can be reproduced with high accuracy as shown in FIGS. 9A, 9B. Therefore, the substances can be specified with high accuracy.

Figure 1:
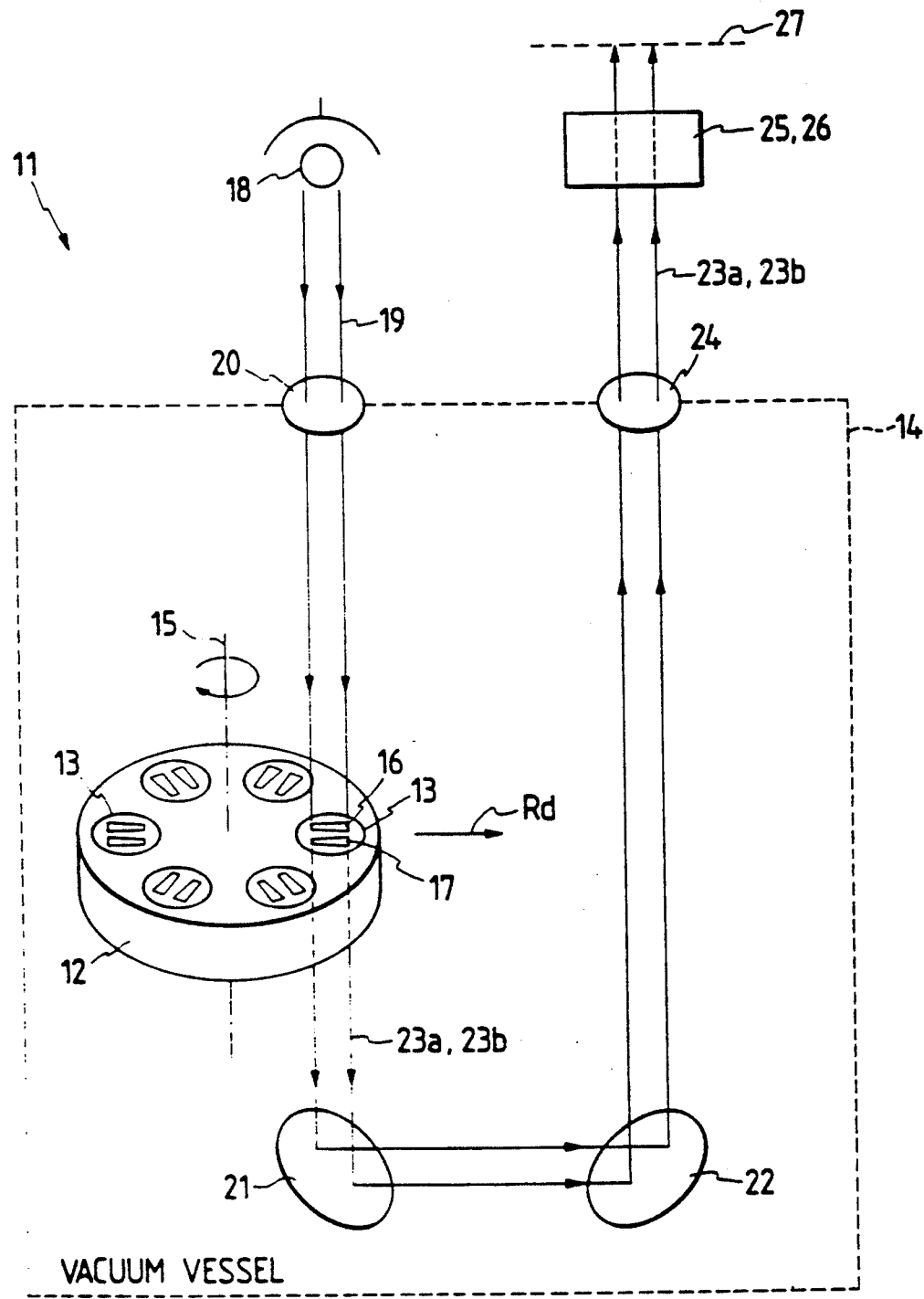
FIG. 1 is a schematic view of a conventional optical system for analyzing samples by utilizing a centrifugal separator.
Figure 2:
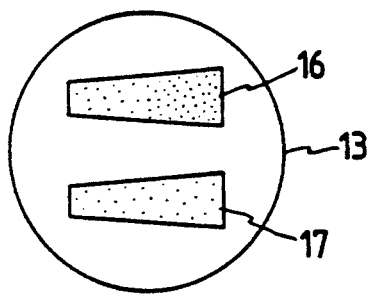
FIG. 2 is a plan view of both a test sample and an reference sample arranged in a sample cell shown in FIG. 1.
Figure 3:
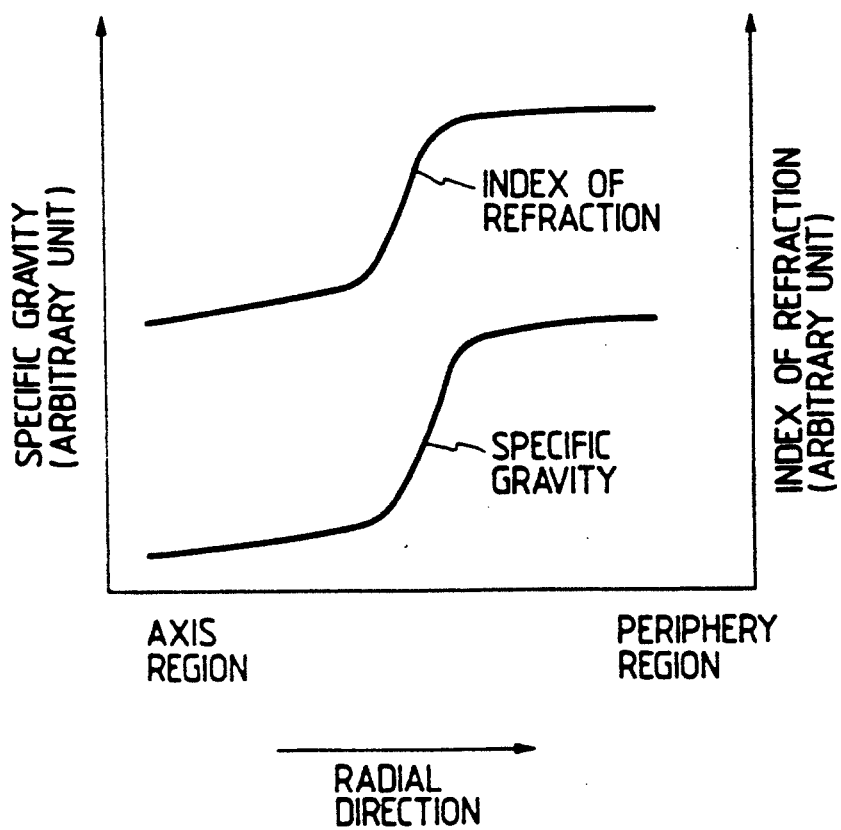
FIG. 3 is a graphic view showing the change of both specific gravity and an index of refraction of the test sample shown in Fig. 2 after the test sample is rotated.
Figure 4:
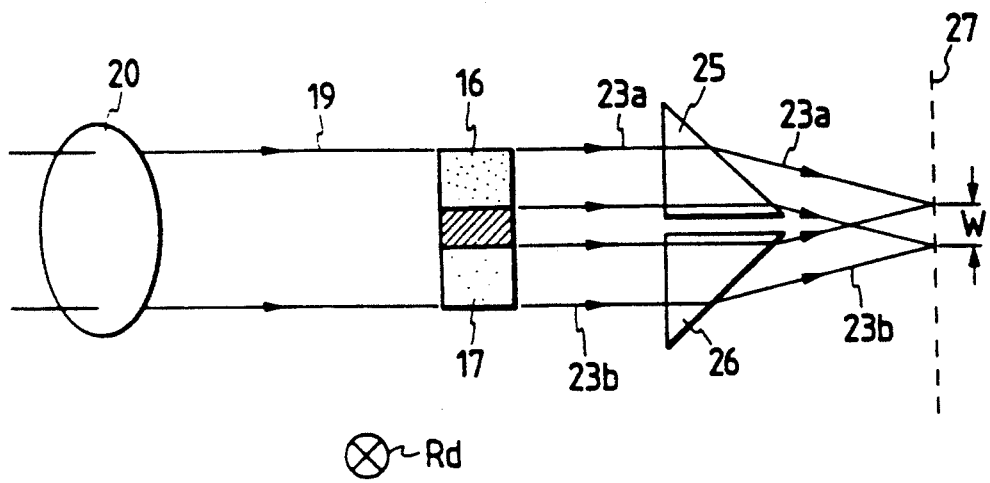
FIG. 4 shows shifted lights refracted by prisms in the conventional optical system shown in FIG. 1 to show the production of interference fringes.
Figure 5:
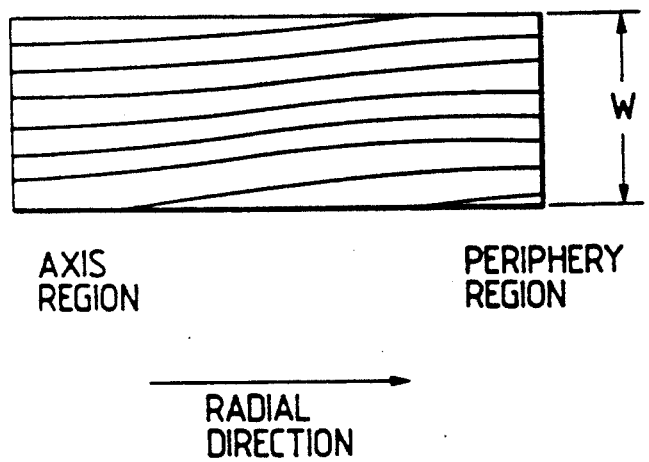
FIG. 5 shows the interference fringes projected on a screen, the interference fringes extending in the radial direction Rd of the sample rotator 12 being shown.

Also, a large number of pieces of data indicating the phase delay differences T2−T1 can be obtained very quickly according to a method for automatically analyzing the test sample 16 by utilizing the optical system 31 shown in FIG. 6 in comparison with a conventional method for taking reading the fringes with the eye to analyze the test sample 16 while utilizing the conventional optical system 11 shown in FIG. 1. In addition, the optical system 31 according to the present invention enable us to obtain sedimentation coefficients of substances in the test sample 16 because the sedimentation coefficients can be obtained by measuring time progress of the data.

Moreover, because the energy intensities Ia, It are automatically transmitted to the signal analyzer 36 each time the sample rotator 12 is rotated in the rotational cycle Rc, and because the difference ΔNr in the index of refraction is automatically analyzed, the substances contained in the test sample 16 can be quickly specified. Therefore a large number of test samples can be analyzed.

Both the test sample 16 and the reference sample 17 are set in the sample cell 13 covered with a quartz glass. Therefore, the phase delay times T1, T2 are undesirably influenced by the thickness of the quartz glass. That is, in cases where the thickness of the quartz glass changes along the radial direction Rd of the sample rotator 12, the difference ΔNr in the index of refraction can not be analyzed with high accuracy. To avoid this drawback, after the samples 16, 17 are set in the sample cell 13, the sample rotator 12 is slowly rotated not to separate the substances contained in the test sample 16. Thereafter, an initial phase delay difference changing along the radial direction Rd of the sample rotator 12 is measured in the same manner as the phase delay difference T2−T1 shown in FIG. 9A. The initial phase delay difference changes with the changes of the thickness of the quartz glass. Thereafter, the sample rotator 12 is rotated at high speed to separate the substances contained in the test sample 16. When the substances are fully separated in the sample cell 13, the phase delay difference T2−T1 is measured before a corrected phase delay difference is obtained by subtracting the initial phase delay difference from the phase delay difference T2−T1.

Therefore, the difference ΔNr in the index of refraction can be analyzed with high accuracy by utilizing the corrected phase delay difference even though the thickness of the quartz glass changes along the radial direction Rd of the sample rotator 12.

As shown in FIG. 6, the He-Ne laser device 32 is utilized to emit a beam having two components of frequencies. However, as is well known, because an acousto-optic modulator has a function to change the laser frequency by applying an acoustic frequency, it is preferred that at least one acousto-optic modulator is utilized together with a laser device which emits a laser beam having a single frequency. In this case, the He-Ne laser device 32 is not required.

Having illustrated and described the principles of our invention in a preferred embodiment thereof, it should be readily apparent to those skilled in the art that the invention can be modified in arrangement and detail without departing from such principles. We claim all modifications coming within the spirit and scope of the accompanying claims.

What is claimed is:

1. An optical system for optically analyzing substances contained in a test sample, comprising:
   light emitting means for emitting a multiplet beam of light which consists of both a light component with a frequency F1 and another light component with another frequency F2;
   a reference sample of which an index of refraction is known;
   sample rotating means, in which the test sample and the reference sample are set for rotating both the test sample and the reference sample to separate the substances contained in the test sample by utilizing a centrifugal force;
   optical means for irradiating the test sample and the reference sample one after another with the multiplet beam of light emitted from the light emitting means while rotating the samples by the sample rotating means to shift a phase of a multiplet beam of light L1 transmitting through the reference sample by an angular value $\phi 1$ depending on an index of refraction of the reference sample and to shift a phase of a multiplet beam of light L2 transmitting through the test sample by another angular value $\phi 2$ depending on the index of refraction of the test sample;
   light mixing means for mixing both the light components with the frequencies F1, F2 in the multiplet beam of light L1 to produce a combined light LC1 and mixing both the light components with the frequencies F1, F2 in the multiplet beam of light L2 to produce another combined light LC2, the phase of the combined light LC1 being shifted by the angular value $\phi 1$ and the phase of the combined light LC2 being shifted by the angular value $\phi 2$; and
   phase difference analyzing means for analyzing a phase difference $\Delta \phi = \phi 2 - \phi 1$ by detecting a differential frequency ΔF contained in both the combined lights LC1, LC2 transmitting from the light mixing means to determine the index of refraction of the test sample separated by the sample rotating means.

2. An optical system according to claim 1 in which both the light component with the frequency F1 and the light component with the frequency F2 are polarized at right angles from each other, and the light mixing means comprises a polarizer in which both the light component with the frequency F1 and the light component with the frequency F2 are polarized in a direction oriented 45 degrees.

3. An optical system according to claim 1 in which the phase difference analyzing means comprises:
   a photo detector for detecting one after another both an energy intensity of the combined light LC1 which oscillates at a phase delay time T1 relating to the angular value $\phi 1$ of the phase shift thereof and another energy intensity of the combined light LC2 which oscillates at a phase delay time T2 relating to the angular value $\phi 2$ of the phase shift thereof and generating both a reference sample signal indicating the energy intensity of the combined light LC1 and a test sample signal indicating the energy intensity of the combined light LC2; and a signal analyzer for analyzing a phase delay difference $T2-T1$ relating to the phase difference $\Delta\phi = \phi 2 - 1$ by utilizing both the reference sample signal and the test sample signal and determining the index of refraction proportional to an product of the phase delay difference $T2-T1$ and the differential frequency $\Delta F$.

4. An optical system according to claim 1 in which the optical means comprises:

a focusing unit for focusing the multiplet beam of light emitted from the light emitting means on the sample rotator to irradiate both the reference sample and the test sample with the multiplet beam of which the diameter is reduced; and a moving unit for moving the focusing unit in a radial direction of the sample rotating means to irradiate the entire test sample with the multiplet beam of light along the radial direction.

5. An optical system according to claim 1 in which the light emitting means is formed of a helium-neon laser device from which a multiplet laser beam is emitted as the multiplet beam of light.

6. An optical system according to claim 1 in which the light emitting means is composed of:

a laser device for emitting a laser beam with a single frequency; and at least one acousto-optic modulator for changing the frequency of the laser beam emitted from the laser device to the multiplet beam of light having a pair of light components with frequencies F1 & F2.

* * * * *